United States Patent
Inget et al.

(10) Patent No.: US 7,346,972 B2
(45) Date of Patent: *Mar. 25, 2008

(54) METHOD OF MAKING A WELDING HELMET

(75) Inventors: Kevin Inget, Imperial Beach, CA (US); Steven Robinson, Long Beach, CA (US)

(73) Assignee: Hoodlums Welding Hoods LLC, Long Beach, CA (US)

(*) Notice: Subject to any disclaimer, the term of this patent is extended or adjusted under 35 U.S.C. 154(b) by 439 days.

This patent is subject to a terminal disclaimer.

(21) Appl. No.: 10/645,446

(22) Filed: Aug. 20, 2003

(65) Prior Publication Data

US 2004/0078859 A1     Apr. 29, 2004

Related U.S. Application Data

(63) Continuation of application No. 10/355,816, filed on Jan. 30, 2003, which is a continuation of application No. 09/772,117, filed on Jan. 26, 2001, now abandoned, and a continuation of application No. 08/843,385, filed on Apr. 14, 1997, now Pat. No. 6,178,552.

(51) Int. Cl.
*B21B 1/46* (2006.01)
*A61F 9/06* (2006.01)

(52) U.S. Cl. ............... 29/527.1; 2/8.2; D29/102
(58) Field of Classification Search ............... 29/527.1; 2/8, 7, 9, 206, 410, 8.2, 8.1; D29/110, 108, D29/102, 106
See application file for complete search history.

(56) References Cited

U.S. PATENT DOCUMENTS

| 1,485,160 | A | * | 2/1924 | Bassan ................... 2/173 |
| 2,249,239 | A | * | 7/1941 | Goldsmith ................ 2/8 |
| 2,786,204 | A | * | 3/1957 | Simpson .................. 2/9 |
| 3,883,982 | A | * | 5/1975 | McClary ................ 446/27 |
| 3,914,796 | A | * | 10/1975 | Barta .................... 2/8 |
| D259,578 | S | * | 6/1981 | Carreiro ............... D21/659 |
| 5,029,342 | A | * | 7/1991 | Stein et al. .............. 2/8 |
| 5,896,579 | A | * | 4/1999 | Johnson et al. ........... 2/8 |
| D425,260 | S | * | 5/2000 | Robinson et al. ...... D29/110 |
| D426,350 | S | * | 6/2000 | Robinson et al. ...... D29/110 |
| 6,178,552 | B1 | * | 1/2001 | Robinson ................ 2/8.1 |
| 2001/0039671 | A1 | * | 11/2001 | Robinson et al. .......... 2/7 |
| 2003/0110548 | A1 | * | 6/2003 | Robinson et al. .......... 2/8 |

* cited by examiner

*Primary Examiner*—John C. Hong
(74) *Attorney, Agent, or Firm*—Lawrence S. Cohen

(57) ABSTRACT

A method of making a welding helmet molded from plastic having animal facial features or animal skull facial features in which a welding helmet lens is attached where the eye feature would be.

4 Claims, 4 Drawing Sheets

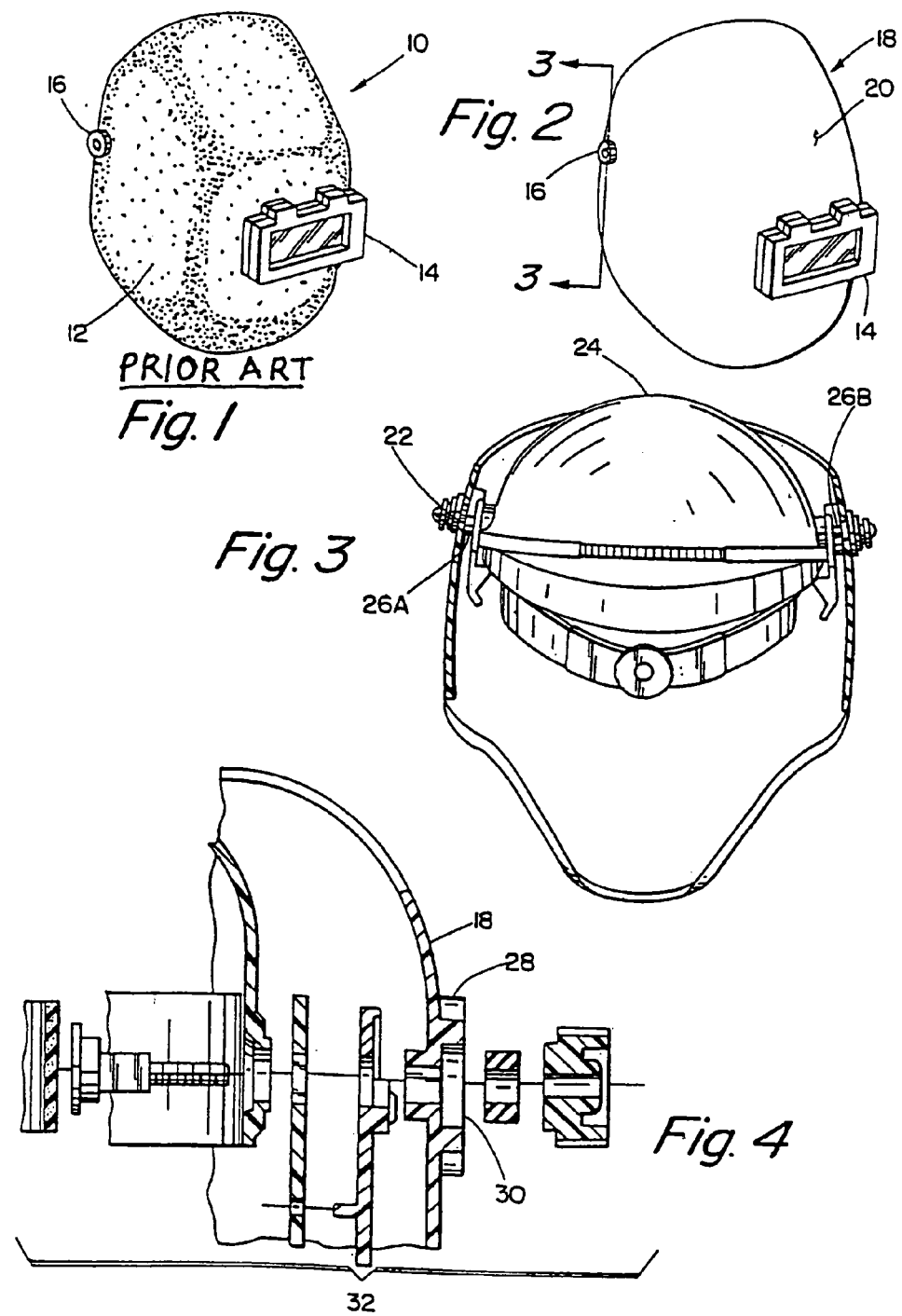

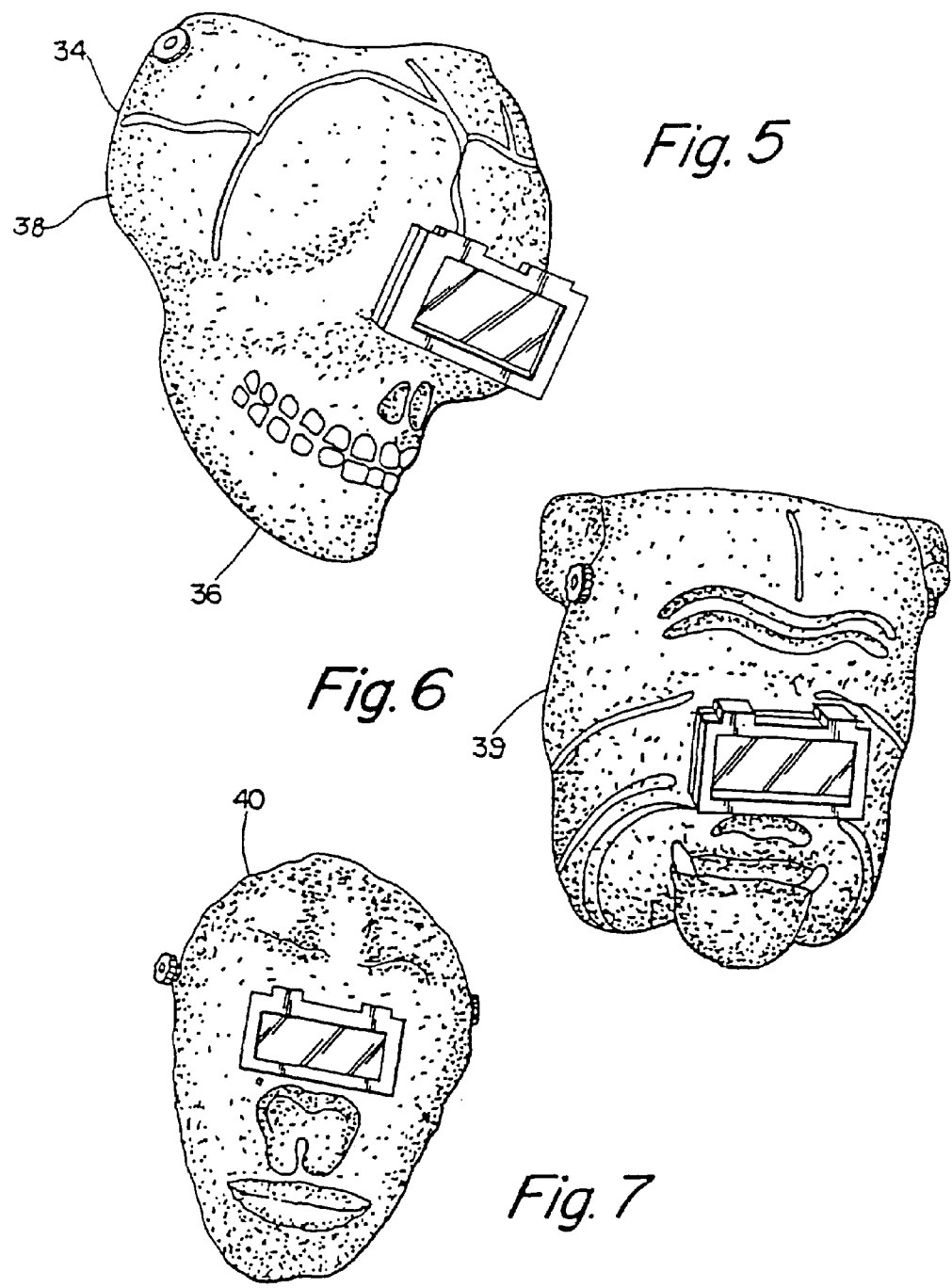

METHOD OF MAKING A WELDING HELMET

RELATED APPLICATIONS

This is a continuation of patent application Ser. No. 10/355,816 filed on Jan. 30, 2003 which is a continuation of patent application Ser. No. 09/772,117 filed on Jan. 26, 2001 now abandoned and of patent application Ser. No. 08/843,385 filed on Apr. 14, 1997 now U.S. Pat. No. 6,178,552 the content all of which is incorporated herein by reference.

FIELD OF THE INVENTION

This invention relates to welding helmets.

BACKGROUND

Welding helmets generally have a smoothly shaped exterior based on their requisite function to protect the welder's head and neck from sparks. Welding helmets have a viewing device which protects the welder's eye from sparks and also provides protection from the damaging brightness of the welding.

Welding helmets are equipped to be able to rotate from an in-use position in front of the welder's face to an open position. The assemblies used for this in general are headgear which the welder wears on his head and which pivotally attach to the helmet. One type is made of straps fitting the welder's head and another fits on a hard hat worn by the welder.

SUMMARY OF THE INVENTION

The invention is a welding helmet made of an appropriate plastic and molded in to the shape of a mammalian head. Particular implementation includes a human skull, a bulldog, and a gorilla. The mammalian head is designed to provide a bib portion to protect the neck and upper chest area and is designated to extend sufficiently to the rear to protect the side of the head and ears from sparks. Also it is shaped to enable the welder to wear a respirator.

BRIEF DESCRIPTION OF DRAWINGS

FIG. 1 shows a welding helmet of the prior art.

FIG. 2 shows a generalized outline of a welding helmet of the present invention.

FIG. 3 is a partial section along 3-3 of FIG. 2 showing how a welding helmet of the invention is a set up for a hard hat.

FIG. 4 shows how a welding helmet of the invention is set up for a strap type headgear assembly.

FIG. 5 is a partial sectional view showing shows a particular embodiment in a human skull form.

FIG. 6 shows a particular embodiment in a bulldog face form.

FIG. 7 shows a particular embodiment in a gorilla form.

DETAILED DESCRIPTION

Figure 8:
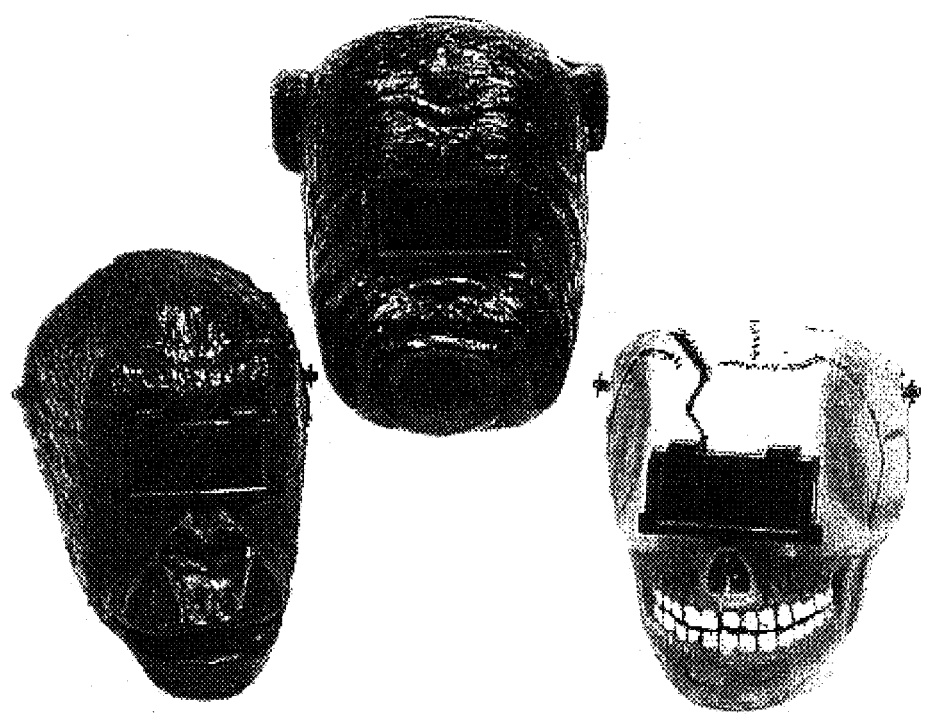
FIG. 8 is a group photograph showing the human skull, bulldog and gorilla welding helmets of FIGS. 5, 6 and 7.

FIG. 1 shows a typical welding helmet 10 of the prior art which has a helmet portion 12, a lens system 14, and pivotable headgear assembly 16 (most of which is not seen). A group of commercially available welding helmets can be found in the 1993 Granger General Catalogue No. 383 at page 1777. Welding helmets are made with a lens system. Sometimes a single lens is built into the helmet. In other models the helmet is adapted to have attached to it a lens retention system made by another manufacturer. These allow exchanging of the lens. A variety of these are seen in the Granger Catalogue.

Welding helmets are also made to accept various headgear assemblies to enable the welder to mount the helmet on his head or on his hard hat, and to allow it to rotate from an in-use position in front of his face to an open position generally over his head. Headgear assemblies made by Huntsman Welding Corp. will work.

One issue in the design and use of welding helmets is to protect the welder's neck and upper chest area from sparks. Therefore some accommodation is made to have the helmet rest or seal against the upper chest such as with a bib portion. Also, welders need protection at the side of their face, even as far back as the ears. This is especially the case where the welder has to maneuver around his work, such as to get his head under a pipe. Therefore the helmet should extend sufficiently to the rear of each side of the welder's head to avoid sparks.

Also, in many cases the welder should wear a respirator while welding.

Therefore the welding helmet must be constructed to accomplish all these requirements.

Consequently the construction of the welding helmets of the present invention are particularly designed to accomplish these requirements.

FIG. 2 shows a generalized welding helmet 18 of the present invention having an exterior surface area 20 to be molded as a mammalian head. It is equipped with a lens 14 and a pivotable headgear assembly 16.

FIG. 3 shows how the welding helmet 18 of the present invention is adapted for a pivotable headgear 22 for use with a hard hat 24. It is not necessary nor intended to show the prior art assemblies in detail. It is sufficient to point out that the welding helmet 18 of the present invention has holes 26A and 26B to receive the parts of a headgear assembly 16 which attaches to a hard hat 18. This mounting of the headgear assembly is generally adaptable for all versions of the mammalian heads, but FIG. 3 shows the human skull version 34.

FIG. 4 shows the welding helmet 18 of the present invention as adapted for conventional headgear of the drop-down limit type which sets the rotation to stop at the right position avoiding the helmet crashing into the welder's chest when it rotates into the in-use. Only one side is shown, the other being a mirror image. The welding helmet 18 has a boss 28 molded into it, or attached, with holes 30 through which the headgear assembly 32 (shown in partial exploded detail) is mounted through the holes 30 to receive the parts of a headgear assembly 20.

Most welding helmets come as purchased with a headgear assembly, but the headgear assembly can be purchased separately and installed in a helmet.

Figure 9:
FIG. 9 is a group photograph showing the human skull, bulldog and gorilla welding helmets of FIGS. 5, 6, 7 and 8 being worn by welders.

FIGS. 5, 8 and 9 shows one embodiment having a human skull shape 34. It is noted that the skull jaw portion 36 extends as a bib would to provide the protection of the neck and upper chest. It also has the portion 38 extending along the side of the head for protection. The skull jaw portion 36 allows a respirator to be worn by the welder.

FIGS. 6, 8 and 9 show the present invention in the form of a bulldog 38. It has all the same features as the human skull of FIGS. 5, 8 and 9.

FIGS. 7, 8 and 9 show the present invention in the form of a gorilla head 40. It has all the same features as the human skull and bulldog of FIGS. 5, 6, 8 and 9.

Although particular embodiments of the invention have been described and illustrated herein, it is recognized that modifications and variations may readily occur to those skilled in the art, and consequently it is intended that the claims be interpreted to cover such modifications and equivalents.

What is claimed is:

1. A method of making a welding helmet having animal skull facial features comprising:

preparing a mold for molding the welding helmet having a reverse structure of an animal skull facial features, which animal skull facial features include a nose feature and a mouth feature and in which there is an area for receiving a welding helmet lens in the area that would otherwise contain eye facial features;

molding a plastic material in the mold to create a welding helmet having the animal skull facial features on the exterior; and fitting a welding helmet lens to the welding helmet in the area for receiving a welding helmet lens.

2. The method of claims 1 in which the animal skull facial features include mammalian facial features.

3. The method of claim 1 in which the animal skull facial features include human facial features.

4. The method of claim 1 in which the animal skull facial features include non-human facial features.

* * * * *